US008653094B2

(12) United States Patent
Bednarz et al.

(10) Patent No.: US 8,653,094 B2
(45) Date of Patent: Feb. 18, 2014

(54) SOLID FORMS OF (S)-ETHYL 2-AMINO-3-(4-(2-AMINO-6-((R)-1-(4-CHLORO-2-(3-METHYL-1H-PYRAZOL-1-YL)PHENYL)-2,2,2-TRIFLUOROETHOXY)-PYRIMIDIN-4-YL)PHENYL)PROPANOATE AND METHODS OF THEIR USE

(75) Inventors: Mark S. Bednarz, Yardley, PA (US); Susan De Paul, Zürich (CH); Ramanaiah C. Kanamarlapudi, Bridgewater, NJ (US); Anett Perlberg, Gunzgen (CH); Haiming Zhang, San Mateo, CA (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 85 days.

(21) Appl. No.: 13/486,103

(22) Filed: Jun. 1, 2012

(65) Prior Publication Data

US 2013/0005754 A1    Jan. 3, 2013

Related U.S. Application Data

(63) Continuation of application No. 12/237,455, filed on Sep. 25, 2008, now Pat. No. 8,193,204.

(60) Provisional application No. 60/975,846, filed on Sep. 28, 2007.

(51) Int. Cl.
*A61K 31/505* (2006.01)

(52) U.S. Cl.
USPC .......................................................... 514/272

(58) Field of Classification Search
USPC .......................................................... 514/272
See application file for complete search history.

(56) References Cited

U.S. PATENT DOCUMENTS

| | | | |
|---|---|---|---|
| 7,553,840 | B2 | 6/2009 | Devasagayaraj |
| 7,723,345 | B2 | 5/2010 | Devasagayaraj |
| 7,968,729 | B2 | 6/2011 | Bednarz |
| 2009/0099206 | A1 | 4/2009 | Iimura |

OTHER PUBLICATIONS

Bastin, R.J., et al., *Org. Process Res. Dev.* 4(5) 427-435 (2000).
Caira, M.R., *Topics Current Chem.* 198:163-208 (1998).
Shi, Z-C., et al., *J. Med. Chem.* 51(13):3684-3687 (2008).
International Search Report for Corresponding Patent Application No, PCT/US2008/077594, dated Nov. 24, 2008.

*Primary Examiner* — James O Wilson
*Assistant Examiner* — Ebenezer O Sackey
(74) *Attorney, Agent, or Firm* — Max Bachrach (57) ABSTRACT

Solid forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate and salts thereof are disclosed.

18 Claims, 4 Drawing Sheets

SOLID FORMS OF (S)-ETHYL 2-AMINO-3-(4-(2-AMINO-6-((R)-1-(4-CHLORO-2-(3-METHYL-1H-PYRAZOL-1-YL)PHENYL)-2,2,2-TRIFLUOROETHOXY)-PYRIMIDIN-4-YL)PHENYL)PROPANOATE AND METHODS OF THEIR USE

This is a continuation of U.S. application Ser. No. 12/237,455, filed Sep. 25, 2008, which claims priority to U.S. provisional patent application No. 60/975,846, filed Sep. 28, 2007, the entireties of which are incorporated herein by reference.

1. FIELD OF THE INVENTION

This invention relates to solid forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate and salts thereof.

2. BACKGROUND OF THE INVENTION

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid (e.g., polymorphic) forms of a new drug substance before products containing it. A. Goho, *Science News* 166(8): 122-123 (2004).

Compounds may exist in one or more crystalline forms, but their existence and characteristics cannot be predicted with any certainty. In addition, no standard procedure exists for the preparation of all possible polymorphic forms of a compound. And even after one polymorph has been identified, the existence and characteristics of other forms can only be determined by additional experimentation. Id.

3. SUMMARY OF THE INVENTION

This invention is directed, in part, to solid forms of the tryptophan hydroxylase inhibitor (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate, and pharmaceutically acceptable salts thereof. Particular solid forms are crystalline.

One embodiment of the invention encompasses pharmaceutical compositions comprising the solid forms described herein.

Another embodiment encompasses methods of treating, managing and preventing various diseases and conditions, which comprise the use of the solid forms described herein.

5. DETAILED DESCRIPTION OF THE INVENTION

This invention is directed, in part, to solid (e.g., crystalline) forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate, and pharmaceutically acceptable salts thereof. The compound is an inhibitor of tryptophan hydroxylase. When administered to animals, the compound decreases peripheral serotonin levels, and may be used to treat a wide range of diseases and disorders. See U.S. patent application No. 60/874,596, filed Dec. 12, 2006.

This invention is also directed to dosage forms comprising solid forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate and pharmaceutically acceptable salts thereof, and to methods of their use.

5.1. Definitions

Unless otherwise indicated, the phrases "disease or disorder mediated by peripheral serotonin" and "disease and disorder mediated by peripheral serotonin" mean a disease and/or disorder having one or more symptoms, the severity of which are affected by peripheral serotonin levels.

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or to prevent its recurrence. A prophylactically effective amount of a compound means an amount of therapeutic agent, alone or in combination with other agents, which provides a prophylactic benefit in the prevention of the disease or condition. The term "prophylactically effective amount" can encompass an amount that improves overall prophylaxis or enhances the prophylactic efficacy of another prophylactic agent.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the terms "treat," "treating" and "treatment" contemplate an action that occurs while a patient is suffering from the specified disease or disorder, which reduces the severity of the disease or disorder or one or more of its symptoms, or retards or slows the progression of the disease or disorder.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

Unless otherwise indicated, a structure or name of a compound or genus of compounds encompasses all forms of that compound or genus of compounds, and all compositions comprising that compound or genus of compounds.

It should also be noted that any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit. Structures that represent compounds with one or more chiral centers, but which do not indicate stereochemistry (e.g., with bolded or dashed lines), encompasses pure stereoisomers and mixtures (e.g., racemic mixtures) thereof. Similarly, names of compounds having one or more chiral centers that do not specify the stereochemistry of those centers encompass pure stereoisomers and mixtures thereof

5.2. Forms of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoate This invention is directed to solid forms of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate:

and pharmaceutically acceptable salts thereof. Particular solid forms are crystalline.

Figure 1:
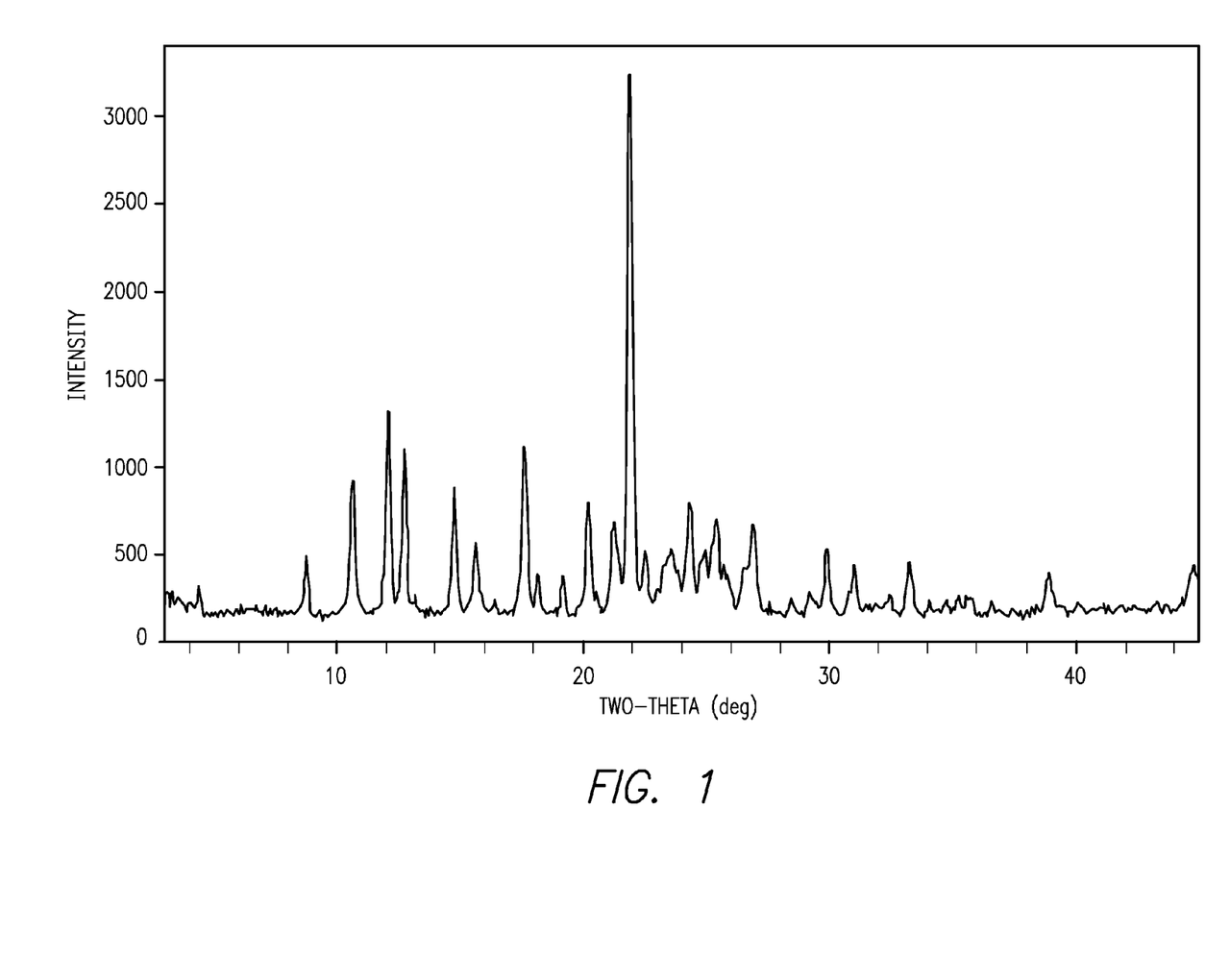
FIG. 1 is an X-ray powder diffraction pattern of a crystalline form of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate. The diffractogram was obtained using a Rigaku MiniFlex diffractometer (copper Kα radiation).

One embodiment of the invention encompasses crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate freebase. One form of this compound has a melting point of about 104° C. as determined by differential scanning calorimetry (DSC) (onset temperature). This form provides an X-ray powder diffraction (XRPD) pattern that contains peaks at about 10.7, 12.2, 12.8, 17.7 and/or 22.0 degrees 2θ. As those skilled in the art are well aware, the relative intensities of peaks in an XRPD pattern of a crystalline material can vary depending on how the sample is prepared and how the data is collected. With this in mind, an example of an XRPD pattern of this crystalline form is provided in FIG. 1.

Figure 2:
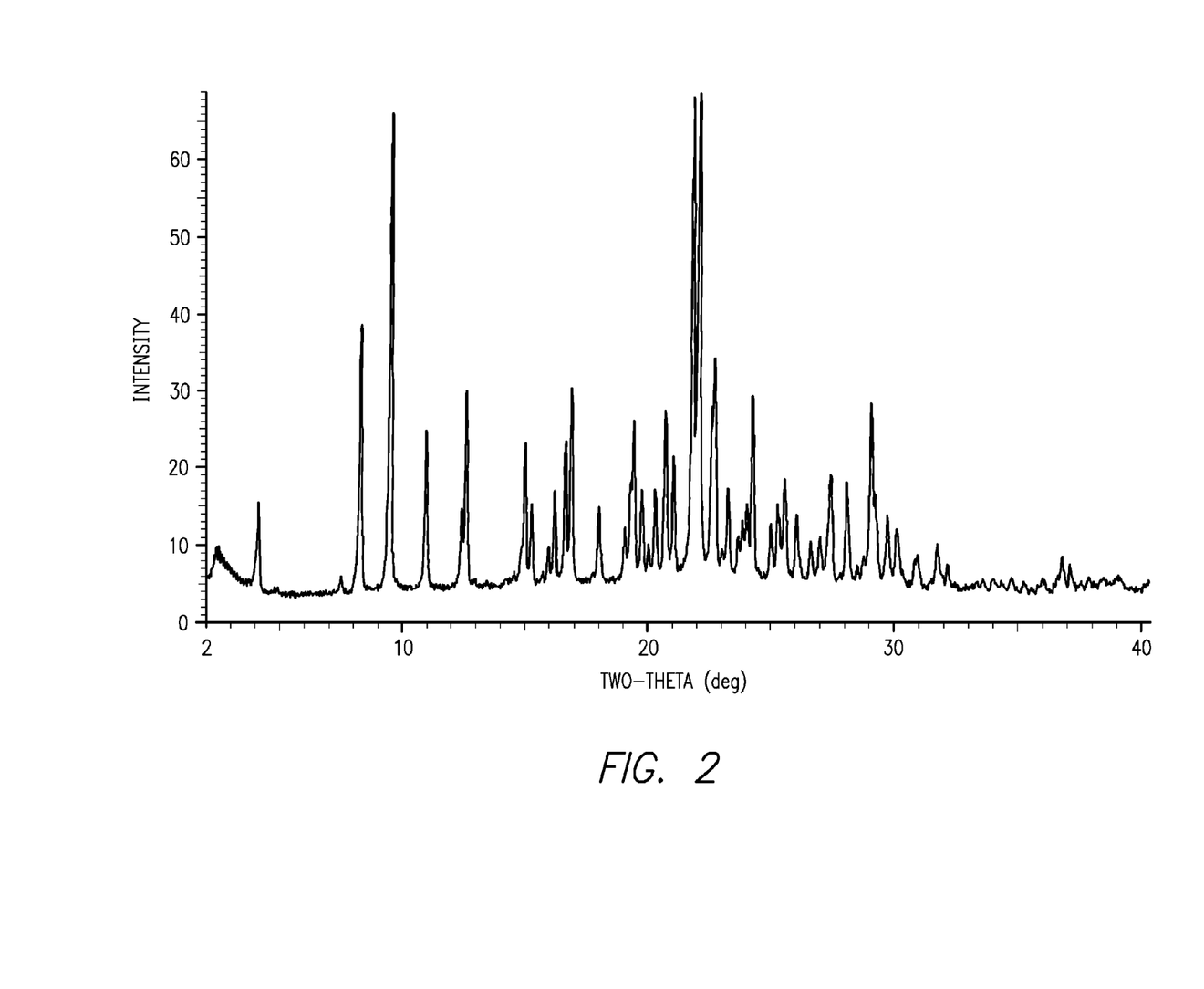
FIG. 2 is an X-ray powder diffraction pattern of a crystalline form of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate hippurate. The diffractogram was obtained using a Bruker D8 Advance (copper Kα radiation).
Figure 3:
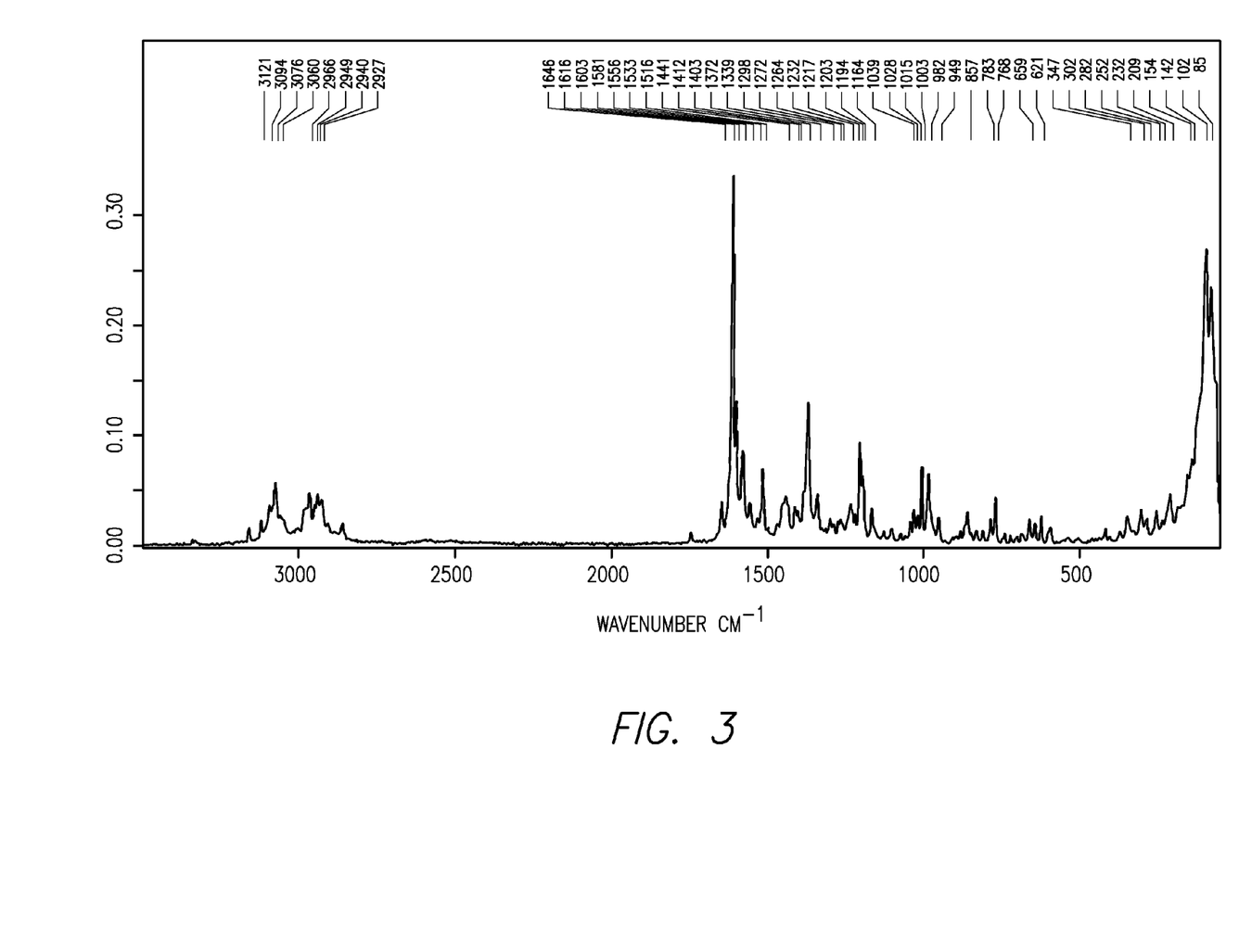
FIG. 3 is a FT-Raman spectrum of a crystalline form of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate hippurate. The spectrum was obtained using a Bruker RFS100 spectrometer (1064 nm excitation).

Another embodiment encompasses crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate hippurate. One form of this compound has a melting point of about 142° C. (DSC onset temperature, with a peak at about 147° C.). This form provides an XRPD pattern that contains peaks at about 8.2, 9.5, 12.6, 16.9, 21.8, 22.0, 22.7, 24.3 and/or 29.1 degrees 2θ. An example of an XRPD pattern of this crystalline form is provided in FIG. 2. An example of an FT-Raman spectrum of this crystalline form is provided in FIG. 3.

Figure 4:
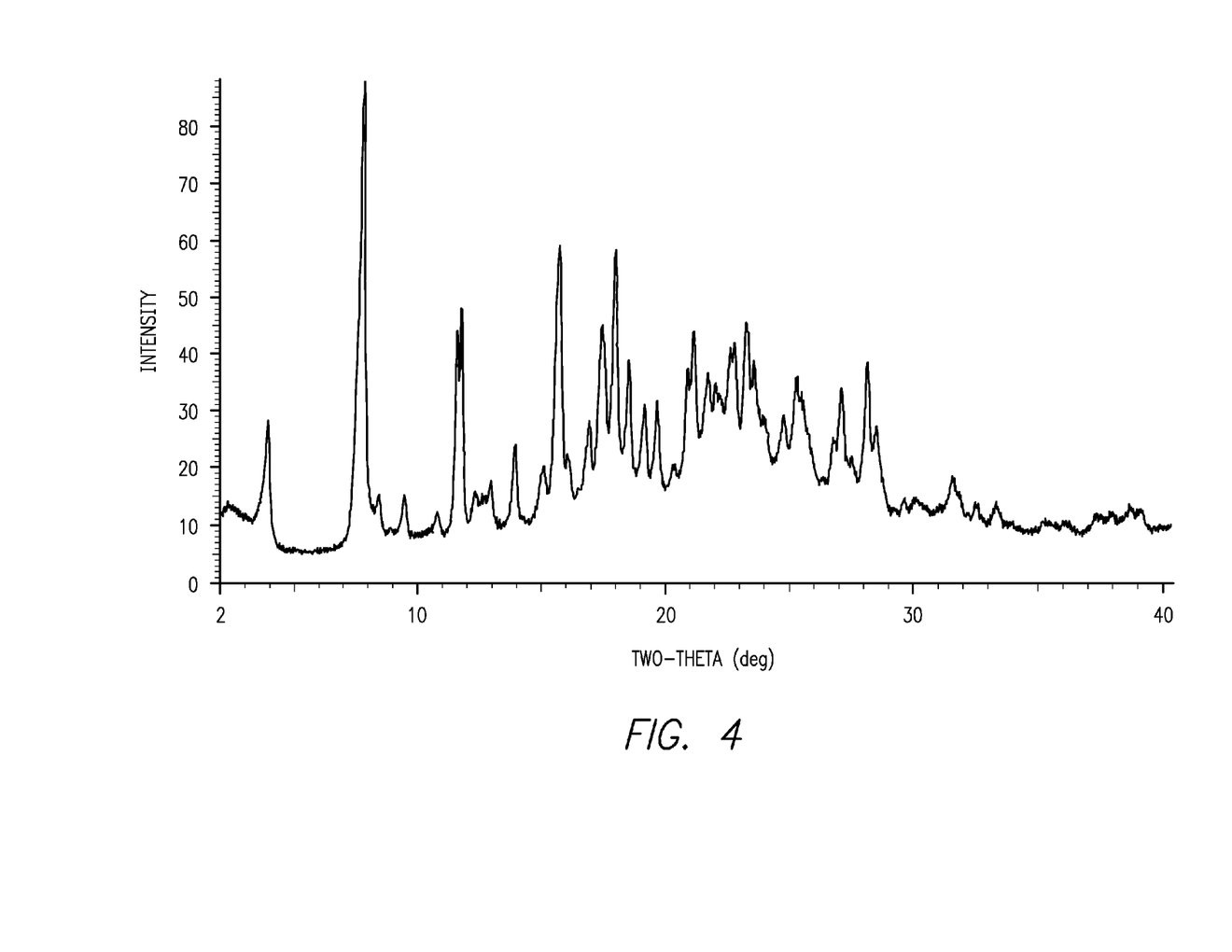
FIG. 4 is an X-ray powder diffraction pattern of a crystalline form of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate succinate. The diffractogram was obtained using a Bruker D8 Advance (copper Kα radiation).

Another embodiment encompasses crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate succinate. One form of this compound provides an XRPD pattern that contains peaks at about 7.7, 11.5, 11.7, 15.7, 17.9, 21.1 and/or 23.2 degrees 2θ. An example of an X-ray powder diffraction pattern of this crystalline form is provided in FIG. 4.

This invention encompasses solids that are mixtures of both amorphous and crystalline forms. Certain such solids comprise crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate or a pharmaceutically acceptable salt thereof in an amount of at least about 50, 75, 80, 85, 90, 95 or 99 weight percent.

Crystalline salts of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate may be prepared by: contacting a solution comprising (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate with pharmaceutically acceptable acid under conditions sufficient to provide a salt of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate; reducing the solubility of the salt in the solution under conditions sufficient to provide a crystalline salt of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate; and isolating the crystalline salt.

The solution may comprise solvents such as isopropyl acetate, ethyl acetate, ethanol, isopropanol, methyl t-butyl ether, and methyl isobutylketone. Particular acids include hippuric and succinic acid.

The solubility of the salt in solution may be reduced by cooling the solution, by increasing the concentration of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate in the solution, or by adding to the solution an anti-solvent (i.e., a solvent in which the salt is insoluble). Heptane is an example of an anti-solvent.

Crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate freebase may be prepared by adding a basic aqueous solution to an organic suspension to provide a mixture having organic and aqueous components, wherein the organic suspension comprises a salt (e.g., a hippurate salt) of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate and an organic solvent; isolating the organic component from the mixture; and cooling and/or concentrating the organic component to provide crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate.

Examples of organic solvents include ethers. Examples of basic aqueous solutions include aqueous solutions of sodium bicarbonate.

5.3. Methods of Treatment

This invention encompasses a method of inhibiting tryptophan hydroxylase (TPH), which comprises contacting TPH with a compound of the invention (i.e., a compound disclosed herein). In a particular method, the TPH is the TPH1 isoform. In a particular method, the inhibition is in vitro. In another, the inhibition is in vivo.

This invention encompasses methods of treating, preventing and managing various diseases and disorders mediated by peripheral serotonin, which comprise inhibiting TPH1 activity in a patient in need of such treatment, prevention or management.

Particular diseases and disorders include carcinoid syndrome and gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional dyspepsia, irritable bowel syndrome (IBS), lactose intolerance, MEN types I and II, Ogilvie's syndrome, Pancreatic Cholera Syndrome, pancreatic insufficiency, pheochromacytoma, scleroderma, somatization disorder, and Zollinger-Ellison Syndrome.

5.4. Pharmaceutical Compositions

This invention encompasses pharmaceutical compositions and dosage forms comprising solid form of the invention. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

6. EXAMPLES

6.1. Preparation of 1-(4-Chloro-2-(3-methyl-1H-pyrazol-1-yl)phenyl)-2,2,2-trifluoroethanone

A 3 L 3-neck round bottom flask equipped with a mechanical stirrer, a temperature controller, and a nitrogen inlet was charged with potassium tert-butoxide (Aldrich 95%, 84.6 g, 0.716 mol) and DMSO (400 mL, 4×) at room temperature and stirred for 15 minutes. To this solution was added pyrazole 2 (59 g, 0.719 mol) followed by a DMSO rinse (50 mL, 0.5×). The resulting orange turbid solution was stirred for 15 min and fluoride 1 (100 g, 0.477 mol) was added followed by a DMSO rinse (50 mL, 0.5×). This mixture was then heated to 50° C. and held for 5 hours at this temperature. After cooling to room temperature, the reaction mixture was diluted with MTBE (750 mL), and water (500 mL) was added to give a brown turbid mixture. After 15 min stirring, the organic layer was separated and sequentially washed with 1 N HCl (250 mL), brine (250 mL), and water (250 mL). Solution assay of organic layer was carried out using GC (conversion>99%, solution yields of 3 and its regioisomer 4 were 83% and 17%, respectively). The MTBE solution was then concentrated under vacuum to a total volume of about 200 mL (KF showed 0.737% water). THF (500 mL) was added, concentrated to 2× solution (KF=0.158%). THF addition-concentration sequence was repeated to give a 2× solution (KF=0.023%) which used directly in the next step.

Analytical samples of compounds 3 and 4 were purified by column chromatography and characterized: Compound 3: white crystals; $^1$H NMR (400 MHz, CDCl$_3$) δ 7.80 (1H, d, J=2.3 Hz), 7.61 (1H, d, J=8.6 Hz), 7.58 (1H, d, J=2.5 Hz), 7.22 (1H, dd, J=8.6, 2.6 Hz), 6.27 (1H, d, J=2.5 Hz), 2.38 (3H, s); $^{13}$C NMR (100 MHz, CDCl$_3$) δ 150.8, 140.6, 134.6, 134.1, 132.0, 129.0, 128.2, 115.4, 107.0, 13.6. Compound 4: white crystals; $^1$H NMR (400 MHz, CDCl$_3$) δ 7.65 (1H, d, J=8.6 Hz), 7.62 (1H, d, J=1.5 Hz), 7.43 (1H, d, J=2.5 Hz), 7.35 (1H, dd, J=8.6, 2.2 Hz), 6.21 (1H, s), 2.19 (3H, s); $^{13}$C NMR (100 MHz, CDCl$_3$) δ 140.6, 140.2, 140.0, 134.1, 133.9, 130.8, 130.2, 120.7, 105.9, 11.4.

The above THF solution was transferred to a jacketed 3 L 3-neck round bottom flask equipped with a mechanical stirrer, a temperature controller, and a nitrogen inlet. After diluted with THF (800 mL), the water content in the solution was checked by KF (0.053%). To the above solution was added a solution of i-PrMgCl in THF (Aldrich 2 M, 286 mL, 0.572 mol) at 0-10° C. over 1 hours. The resulting solution was stirred for 30 min at 10° C. (GC showed the completion of magnesium-bromine exchange reaction). Ethyl trifluoroacetate (74 mL, 0.620 mol) was then added to the Grignard solution between −20 and −10° C. over 45 minutes, slowly warmed to 0° C., and stirred for 30 min at the same temperature. The reaction mixture was poured into 2 N HCl (300 mL) at 0° C., and stirred for 30 minutes at room temperature. The organic layer was diluted with MTBE (500 mL), and washed with brine (250 mL) followed by water (250 mL). Solution assay of organic layer was carried out using GC (Compound 5: 67% solution yield, the corresponding regioisomer 6 was present at about 20% relative to 5). The solution was then concentrated under vacuum to 2× solution. To remove water, THF (500 mL) was added, and evaporated to 2× solution. THF addition-concentration was repeated to give a 2× solution. Heptane (500 mL) was added, concentrated to 2× solution to exchange the solvent for recrystallization. Heptane (500 mL) was again added, concentrated to 3.5× solution.

The 3.5× heptane solution was then transferred to a 1 L 3-neck jacketed round bottom flask equipped with a mechanical stirrer, a temperature controller, and a nitrogen inlet. The solution was heated at 60° C., and the resulting homogeneous solution was slowly (1-2 hours) cooled to room temperature with stirring, further cooled to 0° C. and stirred for 30 min at the same temperature. The crystals were collected and washed with ice-cold heptane (200 mL), dried under vacuum at 50° C. to afford a pale yellow solid (Compound 5, 85.7 g, 99% pure by GC, 62% yield from fluoride 1). $^1$H NMR (400 MHz, CDCl$_3$) δ 7.85 (1H, d, J=2.5 Hz), 7.48 (1H, d, J=1.7 Hz), 7.38 (1H, d, J=8.3 Hz), 7.31 (1H, dd, J=8.1, 1.8 Hz), 6.33 (1H, d, J=2.5 Hz), 2.30 (3H, s); $^{13}$C NMR (100 MHz, CDCl$_3$) δ 184.2 (q, J$_{C-F}$=36.6 Hz), 151.7, 138.7, 138.5, 130.7, 126.4, 125.7, 124.5, 116.8, 116.1 (q, J$_{C-F}$=289.8 Hz), 109.7, 13.0; $^{19}$F NMR (376 MHz, CDCl$_3$) δ=−76.8 (s).

6.2. Preparation of (R)-1-(4-chloro-2-(3-methyl-1H-pyrazol-1-yl)phenyl)-2,2,2-trifluoroethanol

A 3 L 3-neck jacketed round bottom flask equipped with a mechanical stirrer, a temperature controller, and a nitrogen inlet was charged sequentially with dichloro(pentamethylcyclopentadienyl)iridium (III) dimer ([Cp*IrCl$_2$]$_2$, STREM, CAS#: 12354-85-7, 34 mg, 0.043 mmol), (1R,2R)-(−)-N-(4-toluenesulfonyl)-1,2-diphenylethylenediamine (STREM, CAS#: 144222-34-4, 32 mg, 0.087 mmol), and water (400 mL, 4×) at room temperature. The resulting mixture was stirred for 3 hours at 40° C. to give a homogeneous orange solution. To this active catalyst solution was added potassium formate (145.5 g, 1.73 mol) and a solution of the ketone 1-(4-chloro-2-(3-methyl-1H-pyrazol-1-yl)phenyl)-2,2,2-trifluoroethanone (100 g, >99% purity by GC, 0.346 mol) in CH$_3$CN (500 mL, 5×) at 40° C. The reaction mixture was then stirred at 40° C. for 2 h at which time the reaction was determined to be complete by GC. After cooled to 30° C., the aqueous layer (ca. 480 mL) was removed. The organic layer (ca. 600 mL, 6×) was treated with activated carbon (Darco G-60, 20 g, 0.2×) at 45° C. for 2 h and filtered through ¼ inch bed of Celpure P65 (USP-NF, Pharmaceutical grade, Sigma) and washed with CH$_3$CN (200 mL, 2×). The filtrate was concentrated to 250 mL (2.5×) and transferred to a 2 L 3-neck jacketed round bottom flask equipped with a mechanical stirrer and a temperature controller. More CH$_3$CN (50 mL, 0.5×) was added to increase the solution volume to 300 mL (3×). This solution was warmed to 60° C. and water (500 mL, 5×) was added to this solution at the same temperature. After stirred for 15 minutes at 60° C., the resulting emulsion-like milky mixture was slowly cooled to room temperature. The crystals were then filtered at room temperature, and washed with CH$_3$CN/water (1:2, 150 mL, 1.5×). The wet cake (108 g, KF: 8.83%) was dried under vacuum at 45° C. for 4 h to afford the desired alcohol (white solid, 95 g, 94% yield, >99% chemical purity, >99% ee, KF: 0.014%). $^1$H NMR (methanol-d$_4$, 400 MHz) δ 2.19 (br. s., 3H), 5.23 (dd, 6.8 Hz, 7.2 Hz, 1H), 6.19 (d, 2.4 Hz, 1H), 7.29 (d, 2 Hz, 1H), 7.42 (dd, 2.0 Hz, 6.4 Hz, 1H), 7.59 (d, 2.4 Hz, 1H), 7.68 (d, 8.4 Hz, 1H). $^{13}$C NMR (methanol-d$_4$) δ 13.4, 67.2, 108.3, 121.7, 124.5, 127.4, 130.1, 131.9, 134.1, 136.4, 141.6, 152.3. LC/MS: MH$^+$=291.

6.3. Preparation of (S)-methyl 2-(tert-butoxycarbonylamino)-3-(4-(trifluoromethylsulfonyloxy)phenyl)propanoate This compound was prepared based on a literature procedure (Shieh, et al., *J. Org. Chem.* 57:379-381 (1992)). To a solution of Boc-Tyr-OMe (Bachem, California, 100 g, 0.34 mol) and N-methylmorpholine (51 g, 1.5 eq) in dichloromethane (1000 ml) was added triflic anhydride (100 g, 1.05 eq) over 2 hours at −5 to −15° C. The resulting red solution was stirred at −10° C. for 10 minutes. HPLC analysis showed complete disappearance of starting material. The reaction was quenched with 10% citric acid (500 ml). The organic layer was washed with 10% citric acid (500 ml) followed by water (500 ml). The resulting light pink solution was concentrated under reduced pressure to 200 ml. This was diluted with acetonitrile (600 ml) and further concentrated to a 200 g solution. This solution was used in the next step without further purification. Estimated yield was 98% by stripping a sample to dryness to give a low melting pale yellow solid. LC-MS (ESI): MH$^+$=428.0, MNH$_4$$^+$=445.0. $^1$H NMR (CDCl$_3$) δ 7.16 (m, 4H), 4.95 (d, J=7.1 Hz, 1H), 4.53 (m, 1H), 3.64 (s, 3H), 3.10 (dd, J$_1$=5.7 Hz, J$_2$=13.8 Hz, 1H), 2.97 (dd, J$_1$=6.3 Hz, J$_2$=13.6 Hz, 1H), 1.34 (s, 9H). $^{13}$C NMR (CDCl$_3$) δ 172.3, 155.4, 149.0, 137.4, 131.5, 121.7, 119.1 (q, J=321 Hz), 80.54, 54.62, 52.7, 38.3, 28.6. $^{19}$F NMR (CDCl$_3$) δ −73.4.

6.4. Preparation of (S)-2-(tert-butoxycarbonylamino)-3-(4-(4,4,5,5-tetramethyl-1,3,2-dioxaborolan-2-yl)phenyl)propanoic acid This compound was prepared based on a literature procedure (Firooznia, et al., *Tetrahedron Lett.* 40:213-216 (1999)). Bis(pinacolato)diboron (90 g, 1.1 eq), potassium acetate (63 g, 2 eq), tricyclohexylphosphine (2.3 g, 2.5% mol), and palladium acetate (0.72 g, 1 mol %) were mixed in acetonitrile (950 ml) and the resulting mixture stirred at room temperature for 5 minutes. (S)-Methyl 2-(tert-butoxycarbonylamino)-3-(4-(trifluoromethylsulfonyloxy)-phenyl)propanoate solution (190 g, 0.32 mol) was added and the resulting mixture was heated at 80° C. for 1 hour and cooled. HPLC showed complete consumption of the starting material. The reaction mixture was quenched with aqueous potassium bicarbonate solution (57 g in 475 ml water) and resulting mixture was stirred at room temperature for 30 minutes. The mixture was filtered through a pad of cellulose to remove palladium black. A sample of the organic layer was concentrated and purified by column chromatography (gradient: 1:10 to 1:4 ethyl acetate/hexanes) to give (S)-methyl 2-(tert-butoxycarbonylamino)-3-(4-(4,4,5,5-tetramethyl-1,3,2-dioxaborolan-2-yl)phenyl)propanoate as a clear oil. LC-MS (ESI): MH$^+$=406.2, MNH$_4$$^+$=423.2, M$_2$H$^-$=811.5, M$_2$NH$_4$$^+$=428.5. $^1$H NMR (CDCl$_3$) δ 7.76 (d, J=8.1 Hz, 2H), 7.15 (d, J=7.6 Hz, 2H), 4.96 (d, J=7.3 Hz, 1H), 4.60 (m, 1H), 3.72 (s, 3H), 3.13 (m, 2H), 1.44 (s, 9H), 1.36 (s, 12H).

The above organic layer of the ester was stirred with aqueous lithium hydroxide solution (23 g in 500 mL water) at room temperature for 30 minutes. The pH of the resulting slurry was adjusted to about 10 with 6 N hydrochloric acid and filtered. The cake was washed with water (200 mL). Acetonitrile was removed from the filtrate under reduced pressure to give an aqueous slurry (950 mL, additional water was added during distillation). The slurry was filtered through a pad of cellulose and washed with water (200 mL). The filtrate was washed with MTBE (500 mL) and rediluted with 700 mL MTBE. The mixture was acidified to pH about 4.5 with 6 N hydrochloric acid. The organic layer was washed with water (500 mL) and concentrated under reduced pressure to the acid compound as a brown oil (206 g, 95% yield based on estimated purity by NMR). The crude product can be used directly in the following step. Alternatively, the compound can be purified by crystallization from MTBE/heptane to give a white solid, which contains a small amount of the corresponding boronic acid, (S)-3-(4-boronophenyl)-2-(tert-butoxycarbonylamino)propanoic acid. MS (ESI): MH$^+$=392.2, MNH$_4^+$=409.2, M$_2$H$^+$=783.4, M$_2$NH$_4^+$=800.4. $^1$H NMR (CDCl$_3$) δ 7.95 (br s, 1H), 7.76 (d, J=7.8 Hz, 2H), 7.21 (d, J=7.6 Hz, 2H), 5.03 (d, J=7.8 Hz, 1H), 4.62 (m, 1H), 3.18 (m, 2H), 1.43 (s, 9H), 1.35 (s, 12H). $^{13}$C NMR (CDCl$_3$) δ 175.8, 155.7, 139.7, 135.4, 129.2, 84.2, 80.5, 54.5, 38.3, 28.7, 25.2.

6.5. Preparation of (S)-3-(4-(2-amino-6-chloropyrimidin-4-yl)phenyl)-2-(tert-butoxycarbonylamino)propanoic acid To a 2 L 3-neck round bottom flask equipped with a mechanical stirrer and a temperature controller was added (S) 2-(tert-butoxycarbonylamino)-3-(4-(4,4,5,5-tetramethyl-1,3,2-dioxaborolan-2-yl)phenyl)propanoic acid (30.3 g, 0.078 mol), 2-amino-4,6-dichloropyrimidine (38.03 g, 3.0 eq), catalyst POPd6 (0.605 g, 1.0 mol %, CombiPhos Catalysts, Inc., New Jersey) and ethanol (728 mL). To the above stirring slurry was then added aqueous potassium bicarbonate solution (27.85 g, 3.5 eq, in 173 mL H$_2$O) slowly so that CO$_2$ gas evolution was not vigorous. This mixture was heated at 75° C. for 6 hours, at which time HPLC analysis showed greater than 99% conversion of the starting material. Ethanol was removed from the mixture under reduced pressure to give an aqueous slurry (~200 mL), additional H$_2$O (90 mL) was added and the solution was concentrated to ~250 mL. Water (90 mL) was added to the slurry, which was then filtered and washed with water (60 mL×2). The filtrate was extracted with ethyl acetate (150 mL). The aqueous solution was treated with Darco-G60 (6.0 g) at 60° C. for 2h, filtered through celite (Celpure 300, 10g), and diluted with THF (240 mL) and toluene (180 mL). The mixture was slowly added 6N HCl at room temperature until the pH reached 4.0. The organic layer was separated and washed with water (180 mL), and Darco-G60 (6.0 g) was added: the resulting mixture was heated at 60° C. for 2 hours. The solution was cooled to room temperature and filtered through celite (Celpure 300, 10 g). The cake was washed with THF (30 mL×2). The resulting solution was concentrated under vacuum to ~180 mL overall volume, at which point, the product precipitated out of solution. The slurry was then cooled to room temperature, filtered and the cake was washed by toluene (30 mL×2). The solid was oven-dried under vacuum at 50° C. overnight to give 24.0 g of product as a light yellow solid which by $^1$H NMR contained ~8.0 wt % of toluene in 75% (corrected) yield. HPLC showed 91% purity with 9.0% of diacid impurity.

6.6. Alternative Procedure for Preparation of (S)-3-(4-(2-amino-6-chloropyrimidin-4-yl)phenyl)-2-(tert-butoxycarbonylamino)propanoic acid from (S)-2-amino-3-(4-boronophenyl)propanoic acid Using potassium carbonate as Base (S)-2-Amino-3-(4-boronophenyl)propanoic acid (Ryscor Science, Inc., North Carolina, 1.0 g, 4.8 mmol) and potassium carbonate (1.32 g, 2 eq) were mixed in aqueous ethanol (15 ml ethanol and 8 ml water). Di-tert-butyldicarbonate (1.25 g, 1.2 eq) was added in one portion. After 30 min agitation at room temperature, HPLC analysis showed complete consumption of the starting compound and formation of (5)-3-(4-boronophenyl)-2-(tert-butoxycarbonylamino)propanoic acid. The 2-amino-4,6-dichloropyrimidine (1.18 g, 1.5 eq) and the catalyst bis(triphenylphosphine)palladium(II) dichloride (34 mg, 1 mol %) were added and the resulting mixture was heated at 65-70° C. for 3 hours. HPLC analysis showed complete consumption of the intermediate, (S)-3-(4-boronophenyl)-2-(tert-butoxycarbonylamino)propanoic acid. After concentration and filtration, HPLC analysis of the resulting aqueous solution against a standard solution of the title compound showed 1.26 g (67% yield).

6.7. Alternative Procedure for Preparation of (S)-3-(4-(2-amino-6-chloropyrimidin-4-yl)phenyl)-2-(tert-butoxycarbonylamino)propanoic acid from (S)-2-amino-3-(4-boronophenyl)propanoic acid Using potassium carbonate/potassium bicarbonate as Base (S)-2-Amino-3-(4-boronophenyl)propanoic acid (10 g, 48 mmol) and potassium bicarbonate (14.4 g, 3 eq) were mixed in aqueous ethanol (250 ml ethanol and 50 ml water). Di-tert-butyldicarbonate (12.5 g, 1.2 eq) was added in one portion. HPLC analysis indicated that the reaction was not complete after overnight stirring at room temperature Potassium carbonate (6.6 g, 1.0 eq) and additional di-tert-butyldicarbonate (3.1 g, 0.3 eq) were added. After 2.5 hours agitation at room temperature, HPLC analysis showed complete consumption of the starting compound and formation of (S)-3-(4-boronophenyl)-2-(tert-butoxycarbonylamino)propanoic acid. The 2-amino-4,6-dichloropyrimidine (11.8 g, 1.5 eq) and the catalyst bis(triphenylphosphine)-palladium(II) dichloride (0.34 g, 1 mol %) were added and the resulting mixture was heated at 75-80° C. for 2 hours. HPLC analysis showed complete consumption of the intermediate, (S)-3-(4-boronophenyl)-2-(tert-butoxycarbonylamino)propanoic acid. The mixture was concentrated under reduced pressure and filtered. The filtrate was washed with ethyl acetate (200 ml) and diluted with 3:1 THF/MTBE (120 ml). This mixture was acidified to pH about 2.4 by 6 N hydrochloric acid. The organic layer was washed with brine and concentrated under reduced pressure. The residue was precipitated in isopropanol, filtered, and dried at 50° C. under vacuum to give the title compound as an off-white solid (9.0 g, 48% yield). Purity: 92.9% by HPLC analysis. Concentration of the mother liquor yielded and additional 2.2 g off-white powder (12% yield). Purity: 93.6% by HPLC analysis.

6.8. Preparation of (S)-Ethyl 2-amino-3-(4-(2-amino-6(R)-1-(4-chloro-2-(3-methyl-1H-pyrazol-1-yl)phenyl)-2,2,2-trifluoroethoxy)pyrimidin-4-yl)phenyl)propanoate A 500 mL 3-neck round bottom flask equipped with a mechanical stirrer, a temperature controller, and a condenser was charged with the monochloride (S)-3-(4-(2-amino-6-chloropyrimidin-4-yl)phenyl)-2-(tert-butoxycarbonylamino)propanoic acid (20.0 g, 51 mmol), (R)-1-(4-chloro-2-(3-methyl-1H-pyrazol-1-yl)phenyl)-2,2,2-trifluoroethanol (>99% ee, 16.3 g, 56 mmol, 1.1 equiv.), $Cs_2CO_3$ (24.9 g, 76 mmol, 1.5 equiv.), and anhydrous 1,4-dioxane (150 mL, 7.5x, KF=0.003%). The mixture was stirred under nitrogen and the temperature was increased to 100° C. with good stirring. The reaction mixture was stirred at 100° C. for 1 hour and additional $Cs_2CO_3$ (33.2 g, 102 mmol, 2.0 equiv.) was added. The reaction mixture was then stirred for 18 hours at 100° C. The heterogeneous reaction mixture was cooled to 90° C. and water (150 mL, 7.5x) was added with good stirring. The mixture was cooled to room temperature.

To the biphasic solution was added di-tert-butyl dicarbonate (1.11 g, 5.1 mmol, 0.1 equiv.) at room temperature and stirred for 2 h at the same temperature. Toluene (100 mL, 5x) was added, the resulting mixture was stirred for 15 min at room temperature, and the phases were split. Water (100 mL, 5x) was added to the organic layer, and the resulting mixture was stirred for 15 min at room temperature, and the phases were split. The aqueous layer (pH=10.5) was then acidified to pH 7-6 using 6 N HCl at room temperature. EtOAc (100 mL, 5x) was added to this mixture, and further acidification to pH 4 was carried out using 6 N HCl at room temperature with good stirring. After splitting the organic layer, the aqueous layer was extracted with EtOAc (100 mL, 5x). The combined organic layers were washed with brine (100 mL, 5x). The EtOAc layer was then concentrated under vacuum to a total volume of about 40 mL (2x). EtOH (100 mL, 5x) was added, and concentrated to 2x solution. The EtOH (150 mL, 7.5x) addition-concentration sequence was repeated to give a 2x solution of (S)-3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoic acid, which was used directly in the next chemical step. Solution assay showed that the yield was about 75% from (S)-3-(4-(2-amino-6-chloropyrimidin-4-yl)phenyl)-2-(tert-butoxycarbonylamino)propanoic acid assuming that the compound's purity was 100%. Analytically pure Boc-acid was obtained by column chromatography and characterized: $^1$H NMR (DMSO-$d_6$, 400 MHz) δ 1.30 (s, 9H), 2.34 (s, 3H), 2.86 (dd, 1H), 3.07 (dd, 1H), 4.14 (m, 1H), 6.45 (d, 1H), 6.83 (s, 1H), 7.29 (dd, 1H), 7.33 (d, 2H), 7.61 (dd, 1H), 7.75 (d, 1H), 7.99 (d, 2H), 8.21 (d, 1H), 12.5-12.8 (br. s., 1H). $^{13}$C NMR (DMSO-$d_6$) δ 13.99, 13.89, 22.05, 27.78, 28.08, 28.32, 31.21, 36.22, 54.83, 67.41, 67.73, 78.03, 91.15, 107.69, 124.99, 125.18, 126.59, 128.12, 129.30, 130.23, 132.69, 134.65, 135.08, 140.73, 140.89, 150.41, 155.39, 162.76, 166.17, 168.22, 173.40. Anal. Calcd for $C_{30}H_{30}ClF_3N_6O_5$: C, 55.69; hours, 4.67; N, 12.99. Found: C, 55.65; hours, 4.56; N, 12.74.

The above 2x solution was diluted with EtOH (60 mL, 3x) and $CH_3CN$ (100 mL, 5x) at room temperature. TBTU (97% pure, Fluka, 19.7 g, 61 mmol, 1.2 equiv.) and N-methylmorpholine (6.17 mL, 56 mmol, 1.1 equiv.) were added to this solution (KF=0.034%) under nitrogen. The resulting solution was stirred at room temperature for 4 hours. HPLC indicated that the Boc-acid was converted to the Boc-ester (S)-ethyl 3-(4-(2-amino-6-((R)-1-(4-chloro-2-(3-methyl-1H-pyrazol-1-yl)phenyl)-2,2,2-trifluoroethoxy)pyrimidin-4-yl)phenyl)-2-(tert-butoxycarbonylamino)propanoate quantitatively. The reaction mixture was concentrated to about 2x under reduced pressure (40° C. bath temperature, 100 mbar) and diluted with EtOAc (100 mL, 5x) and water (100 mL, 5x). The organic layer was washed with saturated aq. $KHCO_3$ (pH~8.5) (2x100 mL, 5x) and brine (50 mL, 2.5x). This red organic layer was then treated with activated carbon (Darco G-60, 8 g, 0.4x) at 50° C. for 1.5 hours and filtered through ¼ inch bed of Celpure P65 (USP-NF, Pharmaceutical grade, Sigma), and the cake washed with $CH_3CN$ (100 mL, 5x). The resulting yellow-colored filtrate was concentrated to a 2x solution. $CH_3CN$ (100 mL, 5x) was added, and the solution concentrated to a 2x solution. The $CH_3CN$ addition-concentration sequence was repeated to give a 2x $CH_3CN$ solution of the Boc-ester which was used directly in the next step. An analytically pure Boc-ester was obtained by column chromatography and characterized: $^1$H NMR (DMSO-$d_6$, 300 MHz) δ 1.11 (t, J=7.06 Hz, 3H), 1.31 (s, 9H), 2.34 (s, 3H), 2.85-3.08 (m, 2H), 4.1-4.2 (m, 1H), 6.45 (d, J=2.29 Hz, 1H), 6.84 (s, 1H), 7.25-7.41 (m, 3H), 7.66 (dd, J=8.58, 2.10 Hz, 1H) 7.71 (d, J=2.1 Hz, 1H) 7.80 (d, J=8.58 Hz, 1H) 8.0 (d, J=8.39 Hz, 2H) 8.21 (d, J=2.29 Hz, 1H). $^{13}$C NMR (DMSO-$d_6$) δ 13.2, 14.0, 22.1, 24.7, 27.7, 28.0, 28.3, 28.4, 31.2, 33.9, 34.1, 36.2, 36.6, 55.0, 56.3, 60.4, 67.1, 67.4, 67.7, 68.0, 78.2, 78.5, 91.1, 107.7, 122.1, 125.0, 125.2, 126.6, 127.7, 128.1, 129.3, 130.2, 132.7, 134.7, 135.1, 140.4, 140.7, 150.4, 154.2, 155.3, 162.8, 166.1, 168.2, 171.9. Anal. Calcd for $C_{32}H_{34}ClF_3N_6O_5$: C, 56.93; hours, 5.08; N, 12.45. Found: C, 57.20; hours, 4.86; N, 12.21

The above 2x solution was diluted with additional $CH_3CN$ (160 mL, 8x) at room temperature. Methanesulfonic acid (18.4 mL, 255 mmol) was added to this solution (KF=0.005%) at room temperature, and stirred at 45° C. for 1 hour at which time HPLC indicated that the de-Boc reaction is complete. The reaction mixture was concentrated to 2x, cooled to 0-5° C., and diluted with ice-cold water (100 mL, 5x) and this aqueous solution was washed with cold isopropyl acetate twice (IPAc, 100 mL, 5x and 50 mL, 2.5x). The aqueous layer was then basified to pH=6 with 20% aq. $Na_2CO_3$ at 5° C. with stirring. IPAc (100 mL, 5x) was added to this mixture, and further basification to pH 8.5 was carried out using 20% aq. $Na_2CO_3$ at room temperature with good stirring. After splitting the organic layer, the aqueous layer was extracted with IPAc (50 mL, 2.5x). The combined cloudy organic layers were concentrated to a 2x solution. IPAc (100 mL, 5x) was added, and the mixture was concentrated to a 2x solution which contained inorganic salts. The mixture was filtered, and the solids washed with IPAc (100 mL, 5x), and the filtrate concentrated to a 2x solution. HPLC assay of this clear IPAc solution showed 20.8 g of the title compound (36 mmol, >99% are by HPLC, 71% solution yield).

Analytically pure title compound was obtained by column chromatography and characterized: $^1$H NMR (DMSO-d6, 400 MHz) δ 1.15 (t, J=7.07 Hz, 3H), 2.39 (s, 3H), 2.50 (m, 2H), 3.63 (t, J=6.82 Hz, 1H), 4.07(q, J=7.07, 14.5 Hz, 2H), 6.50(d, J=2.27 Hz, 2H), 6.87 (s, 1H), 7.33 (m, 3H), 7.65 (dd, J=8.59, 2.27 Hz, 1H), 7.71 (d, J=2.27 Hz, 1H), 7.81(d, J=8.59 Hz, 1H) 8.01 (d, J=8.08 Hz, 2H), 8.26 (d, J=2.27 Hz, 1H). $^{13}$C NMR (DMSO-d6) δ 13.4, 13.9, 18.5, 21.0, 21.5, 25.4, 55.6, 56.0, 59.9, 66.9, 67.1, 67.4, 67.7, 68.0, 91.1, 107.7, 122.1, 124.9, 125.0, 125.2, 126.5, 127.7, 128.1, 129.4, 130.2, 132.7, 134.6, 135.1, 140.7, 140.9, 150.4, 162.8, 166.2, 168.2, 174.8. Anal. Calcd for C27H26ClF3N6O3: C, 56.40; hours, 4.56; N, 14.62. Found: C, 56.51; hours, 4.52; N, 14.51.

6.9. Preparation of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate Hippurate The 2× IPAc solution of (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate was added to a thin slurry of hippuric acid (6.49 g, 36 mol, 1.0 equiv.) in IPAc (208 mL, 10×) and EtOH (42 mL, 2×) at 60° C. The clear yellow solution was then cooled to 50° C., at which time seeding was added and stirred for 1 h at the same temperature. The suspension was then slowly cooled to room temperature and stirred for 14 h at room temperature. The solids were filtered, washed with ice-cold IPAc (0-5° C., 42 mL, 2×) and dried under vacuum at 50° C. overnight to afford a white solid (19.0 g, 69% yield). M.p.: 145° C. (DSC onset temperature)

6.10. Preparation of Crystalline(S)-Ethyl 2-amino-3-(4-(2-amino-64(R)-1-(4-chloro-2-(3-methyl-1H-pyrazol-1-yl)phenyl)-2,2,2-trifluoroethoxy)pyrimidin-4-yl)phenyl)propanoate Freebase A total of 35.79 g hippurate salt was suspended in 350 mL methyl tert-butyl ether. The pH of this stirring suspension was adjusted to pH 9.6 by adding 125 mL 10% w/v aq sodium carbonate. After 1.5 hours, the upper organic phase was drawn off and washed with 100 mL brine. Concentration of the organic layer gave 28.47 g of a pale orange yellow glassy oil which crystallized on standing over a weekend. The solids were broken up and triturated with 400 mL heptane at about 45° C. After cooling to ambient temperature, the suspended crystals were isolated by filtration, washed with heptane, and dried in vacuo at about 40° C. to afford 25.49 g of the title compound as a crystalline white powder. M.p.: 104° C. (DSC onset temperature).

6.11. Preparation of Crystalline(S)-Ethyl 2-amino-3-(4-(2-amino-64(R)-1-(4-chloro-2-(3-methyl-1H-pyrazol-1-yl)phenyl)-2,2,2-trifluoroethoxy)pyrimidin-4-yl)phenyl)propanoate Succinate (S)-Ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate (80.2 mg) was suspended in 0.2 mL THF. A solution of succinic acid in THF (16.4 mg in 0.372 mL solution, 1 eq.) was added to this solution while stirring with a magnetic stirrer. Heptane (1.8 mL) was added dropwise, and the resulting suspension was stirred for 1.5 hours. Additional heptane (1 mL) was added, and the suspension was stirred at room temperature overnight (19.5 hours). The white solid was isolated by filter centrifugation (15000 rpm, 5 minutes., 0.22 µm PVDF membrane).

All references (e.g., patents and patent applications) cited above are incorporated herein by reference in their entireties.

What is claimed is:

1. A method of treating or managing a disease or disorder mediated by peripheral serotonin, which comprises administering to a patient in need of such treatment, or management a therapeutically effective amount of a compound, which is crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate or a pharmaceutically acceptable salt thereof.

2. The method of claim 1, wherein the disease or disorder is carcinoid syndrome.

3. The method of claim 1, wherein the disease or disorder is a gastrointestinal disease or disorder.

4. The method of claim 3, wherein the disease or disorder is irritable bowel syndrome.

5. The method of claim 1, wherein the disease or disorder is Crohn's disease.

6. The method of claim 1, wherein the compound is crystalline (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate.

7. The method of claim 6, wherein the compound has a melting point of about 104° C.

8. The method of claim 6, wherein the compound has an X-ray powder diffraction pattern with peaks at one or more of about 10.7, 12.2, 12.8, 17.7 and/or 22.0 degrees 2θ.

9. The method of claim 6, wherein the compound has an X-ray powder diffraction pattern that is substantially the same as that shown in FIG. 1.

10. The method of claim 1, wherein the compound is a crystalline salt of (S)-ethyl 2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoate.

11. The method of claim 10, wherein the compound is a hippurate salt.

12. The method of claim 11, wherein the compound has a melting point of about 145° C.

13. The method of claim 11, wherein the compound has an X-ray powder diffraction pattern comprising peaks at one or more of about 8.2, 9.5, 12.6, 16.9, 21.8, 22.0, 22.7, 24.3 and/or 29.1 degrees 2θ.

14. The method of claim 11, wherein the compound has an X-ray powder diffraction pattern that is substantially the same as that shown in FIG. 2.

15. The method of claim 11, wherein the compound has a Raman spectrum that is substantially the same as that shown in FIG. 3.

16. The method of claim 10, wherein the compound is a succinate salt.

17. The method of claim 16, wherein the compound has an X-ray powder diffraction pattern comprising peaks at one or more of about 7.7, 11.5, 11.7, 15.7, 17.9, 21.1 and/or 23.2 degrees 2θ.

18. The method of claim 16, wherein the compound has an X-ray powder diffraction pattern that is substantially the same as that shown in FIG. 4.

* * * * *